United States Patent
Vonk et al.

(10) Patent No.: US 7,369,919 B2
(45) Date of Patent: May 6, 2008

(54) MEDICATION ADHERENCE SYSTEM

(76) Inventors: Glenn P. Vonk, 2717 Piney Grove, Wilbon Rd., Fuguay-Varina, NC (US) 27526; Richard C. Rumbaugh, 134 Heather Ridge Rd., Durham, NC (US) 27712; Colleen Ryan, 2217 Recodo Ct., Carlsbad, CA (US) 92009

( * ) Notice: Subject to any disclaimer, the term of this patent is extended or adjusted under 35 U.S.C. 154(b) by 213 days.

(21) Appl. No.: 10/497,310

(22) PCT Filed: Nov. 26, 2002

(86) PCT No.: PCT/US02/37804

§ 371 (c)(1),
(2), (4) Date: Jan. 26, 2005

(87) PCT Pub. No.: WO03/048919

PCT Pub. Date: Jun. 12, 2003

(65) Prior Publication Data

US 2006/0058917 A1 Mar. 16, 2006

(51) Int. Cl.
*G06F 17/00* (2006.01)
(52) U.S. Cl. .................. 700/236; 700/237; 700/242
(58) Field of Classification Search ............... 700/236, 700/237, 242
See application file for complete search history.

(56) References Cited

U.S. PATENT DOCUMENTS

| | | |
|---|---|---|
| 4,473,156 A | 9/1984 | Martia |
| 4,731,726 A | 3/1988 | Allen, III |
| 4,768,177 A | 8/1988 | Kehr et al. |
| 5,088,056 A | 2/1992 | McIntosh et al. |
| 5,200,891 A | 4/1993 | Kehr et al. |
| 5,289,157 A | 2/1994 | Rudick et al. |
| 5,408,443 A | 4/1995 | Weinberger |

(Continued)

FOREIGN PATENT DOCUMENTS

WO    WO 01/47466 A1    7/2001

(Continued)

OTHER PUBLICATIONS

"Maximizing Drug Compliance in the Elderly" Ennis, K.J. and Riechard, R.A., Postgraduate Medicine, 1997 vol. 102, p. 211-224.

(Continued)

*Primary Examiner*—Gene O. Crawford
*Assistant Examiner*—Timothy R Waggoner
(74) *Attorney, Agent, or Firm*—Roylance, Abrams, Berdo and Goodman, LLP (57) ABSTRACT

A system comprising a medication tray (10) and a docking station (20) for facilitating effective self-management of medication treatment by patients is provided. The medication tray (10) accepts medication filled containers (30) and mates with the docking station (20). The medication tray (10) receives prescription data at the time the medication tray (10) accepts the medication filled containers (30), which is then downloaded to the docking station (20). The docking station (20) monitors and reports to third parties, via a network (160), a patient's compliance with various medication treatment regimens. Medication containers (30) are provided with low bit tags (35) that provide container presence information to the docking station (20). The docking station (20) provides visual and/or audio signals regarding prescription data to a patient. The docking station (20) can query patients and appliances regarding patient's medication usage and health status.

16 Claims, 6 Drawing Sheets

U.S. PATENT DOCUMENTS

| | | | |
|---|---|---|---|
| 5,468,948 A * | 11/1995 | Koenck et al. ........ 235/472.01 |
| 5,619,991 A | 4/1997 | Sloane |
| 5,642,731 A | 7/1997 | Kehr |
| 5,752,235 A | 5/1998 | Kehr et al. |
| 5,774,865 A | 6/1998 | Glynn |
| 5,852,590 A | 12/1998 | de la Huerga |
| 5,883,576 A | 3/1999 | de la Huerga |
| 5,897,493 A | 4/1999 | Brown |
| 5,899,855 A | 5/1999 | Brown |
| 5,954,641 A | 9/1999 | Kehr et al. |
| 5,960,085 A | 9/1999 | de la Huerga |
| 5,997,476 A | 12/1999 | Brown |
| 6,021,392 A | 2/2000 | Lester et al. |
| 6,024,699 A | 2/2000 | Surwit et al. |
| 6,032,155 A | 2/2000 | De La Huerga |
| 6,075,755 A * | 6/2000 | Zarchan ........................ 221/3 |
| 6,101,478 A | 8/2000 | Brown |
| 6,102,855 A | 8/2000 | Kehr et al. |
| 6,150,942 A | 11/2000 | O'Brien |
| 6,161,095 A | 12/2000 | Brown |
| 6,168,563 B1 | 1/2001 | Brown |
| 6,255,951 B1 | 7/2001 | de la Huerga |
| 6,259,654 B1 | 7/2001 | de la Huerga |
| 6,285,916 B1 * | 9/2001 | Kadaba et al. .............. 700/222 |
| 6,294,999 B1 * | 9/2001 | Yarin et al. .................... 705/2 |
| 6,346,886 B1 | 2/2002 | de la Huerga |
| 6,366,206 B1 | 4/2002 | Ishikawa et al. |
| 6,380,858 B1 | 4/2002 | Yarin et al. |
| 6,408,330 B1 | 6/2002 | de la Huerga |
| 6,529,446 B1 | 3/2003 | de la Huerga |
| 6,636,780 B1 * | 10/2003 | Haitin et al. ................. 700/236 |
| 2001/0017817 A1 | 8/2001 | de la Huerga |
| 2001/0028308 A1 | 10/2001 | de la Huerga |
| 2002/0027507 A1 | 3/2002 | Yarin et al. |
| 2002/0067270 A1 | 6/2002 | Yarin et al. |
| 2002/0084904 A1 | 7/2002 | de la Huerga |
| 2002/0116509 A1 | 8/2002 | De La Huerga |

OTHER PUBLICATIONS

APREX website printout, 1 pp., Nov. 27, 2001.
AARDEX Ltd, "MEMS IV Monitors" website printout, 1 pp, Nov. 27, 2001.
AARDEX Ltd, "MEMS V Monitors" website printout, 1 pp, Nov. 27, 2001.
www.epill.com, "Never Forget Your medicine Again", 3 pp., Nov. 27, 2001.
Med-eMonitor, MEDGlider, 3 pp, Nov. 27, 2001.

* cited by examiner

MEDICATION ADHERENCE SYSTEM

FIELD OF THE INVENTION

The present invention relates to a medication adherence system comprising a smart medication tray and a cooperating docking station for assisting patients in adhering to medication schedules.

BACKGROUND OF THE INVENTION

Many patients with chronic conditions have difficulty adhering to prescribed therapies. In general, the more medications taken and the more times each day that patients must use various therapies, the more likely there will be a medication error. Often patients have co-morbid conditions that interfere with their adherence to medication regimens. These conditions may include diabetes and associated complications such as blindness or lack of mobility, various neurological conditions and dementias, arthritis and associated difficulties in manipulating devices, and other debilitating conditions. The interactions of various co-morbidities can bring additional complexity and dynamism to medication regimens. Cognition also generally declines with age. Consequently, elderly patients may experience difficulty organizing their medications and remembering to take them as prescribed. Frequently, patients do not know what medications they are taking or why these medications are useful. These patients may lose motivation to adhere to their prescribed regimens. Often patients stop medications because they experience adverse side effects. Adjusting the medication dose, or switching to an alternative medication, can often minimize these side effects while maintaining significant health benefits. These problems are widely recognized, but there have been no cost-effective solutions to date.

Several solutions to the above problems have been proposed. One category of devices monitors when the cap of a prescription pill bottle has been removed. This information is stored electronically and may be uploaded to a data network using a remote docking station. This method is convenient for a few medications, but difficult with many medications. In addition, the individual devices are relatively expensive. Aprex's (www.aardex.com) smart pill bottle cap is an example of such a device.

Another category of devices includes vending machine concepts. These devices contain a plurality of medications and dispense them at an appropriate time specified by internal software and hardware systems. Few of these devices have been commercialized since they are relatively expensive to manufacture and have limited capacity for various medications. The reliability of these devices in a remote setting is also questionable. The e-pill MD.2 Monitored Automatic Medication Dispenser (www.epill.com) is an example of such a device, although it only dispenses a single medication container.

A third category of devices uses a tray which is inserted into a portable device. These trays may be filled with medications as needed. The MEDGlider (www.informedix.com) is an example of such a device. This device has limited capacity for patients with chronic conditions. Also, since the medication tray is not identified to the main device, there may be confusion over which tray should be placed in the device. Finally, this devices does not include a medication package that contains all the medications to be taken at a single time. That is, patients using this device must remove each medication sequentially as they are reminded to by systems contained in the main device. This long sequence of taking multiple medications will limit the number of patients willing to use this device to those with relatively simple conditions, good cognition and strong motivation.

A fourth category of medication management devices is an organizer/reminder device. Typically, these devices use small trays or compartments and are self-programmed by patients to remind them to take medications at a specific time. Typically, the patient also fills the device as needed. When patients either self-program or self-fill the device, errors can occur. These errors become more common as the complexity of the medication regimen increases. Conventional organizer/reminder devices do not prevent these kinds of errors. Since these devices do not record medication usage, and are not connected to a support service, they have limited positive effect on medication adherence.

A fifth category of devices includes pill containers which contain radio frequency (RF) tags that are sensed on a platform. An example of such a device is disclosed in commonly-assigned U.S. Pat. No. 6,294,999, incorporated by reference herein. These devices may contain a large number of pill containers on the device, but each pill container is placed individually on the device. This creates some difficulty for the patients using these devices since they have to place a large number of containers randomly on the device; there is also some potential that some containers will be lost. An additional limitation of this approach is the need to fill a large number of medication containers with a number of different medications all taken at a specific time by the patient. These containers must be filled with a high degree of accuracy and precision. In addition, labeling of containers that contain many medications is difficult since the containers may not be large enough to hold a legible label listing required information for each medication in the pill container.

Other commonly-assigned U.S. patents and published international (PCT) applications disclosing related subject matter are listed below. Each of the listed patents and published applications is incorporated by reference herein.

```
4,731,726
4,768,177
5,200,891
5,642,731
5,897,493
5,954,641
5,997,476
6,024,699
6,101,478
6,102,855
6,161,095
6,168,563
WO 99/18532
WO 99/46718
WO 00/32098
```

The prior art does not satisfy the unmet needs for medication adherence as described above. Solutions to these needs form the objects of the present invention.

SUMMARY OF THE INVENTION

The present invention provides a device and method to assist people who manage therapies at remote locations, especially medications. In a preferred embodiment of the invention, these medications are placed into a smart medication tray. information about the medications, their location on the tray, and when they are to be taken is transmitted to, and stored within, the smart medication tray. This medication tray can, in turn, be placed into a docking station. The docking station contains additional sensing elements so that it can both read the information embedded in the smart tray, and detect which medications have been removed from the tray. The docking station can interact with patients using audio, visual and tactile means, and communicate with remote information services over a network. The docking station can utilize the information embedded in the smart medication tray and additional sensory elements to remind patients when to take their medications, can provide information about the medications, can monitor adherence to the prescribed therapies, and can transmit this information to a remote support service that can further assist patients in managing their conditions.

BRIEF DESCRIPTION OF THE DRAWINGS

The various objects, advantages and novel features of the present invention will be more readily appreciated from the following detailed description when read in conjunction with the attached drawing, in which.

DETAILED DESCRIPTION OF THE PREFERRED EMBODIMENTS

The various features of the preferred embodiments will now be described with reference to the drawing figures, in which like parts are identified with the same reference characters. The following description of the presently contemplated best mode of practicing the invention is not to be taken in a limiting sense, but is provided merely for the purpose of describing the general principles of the invention.

Figure 1:
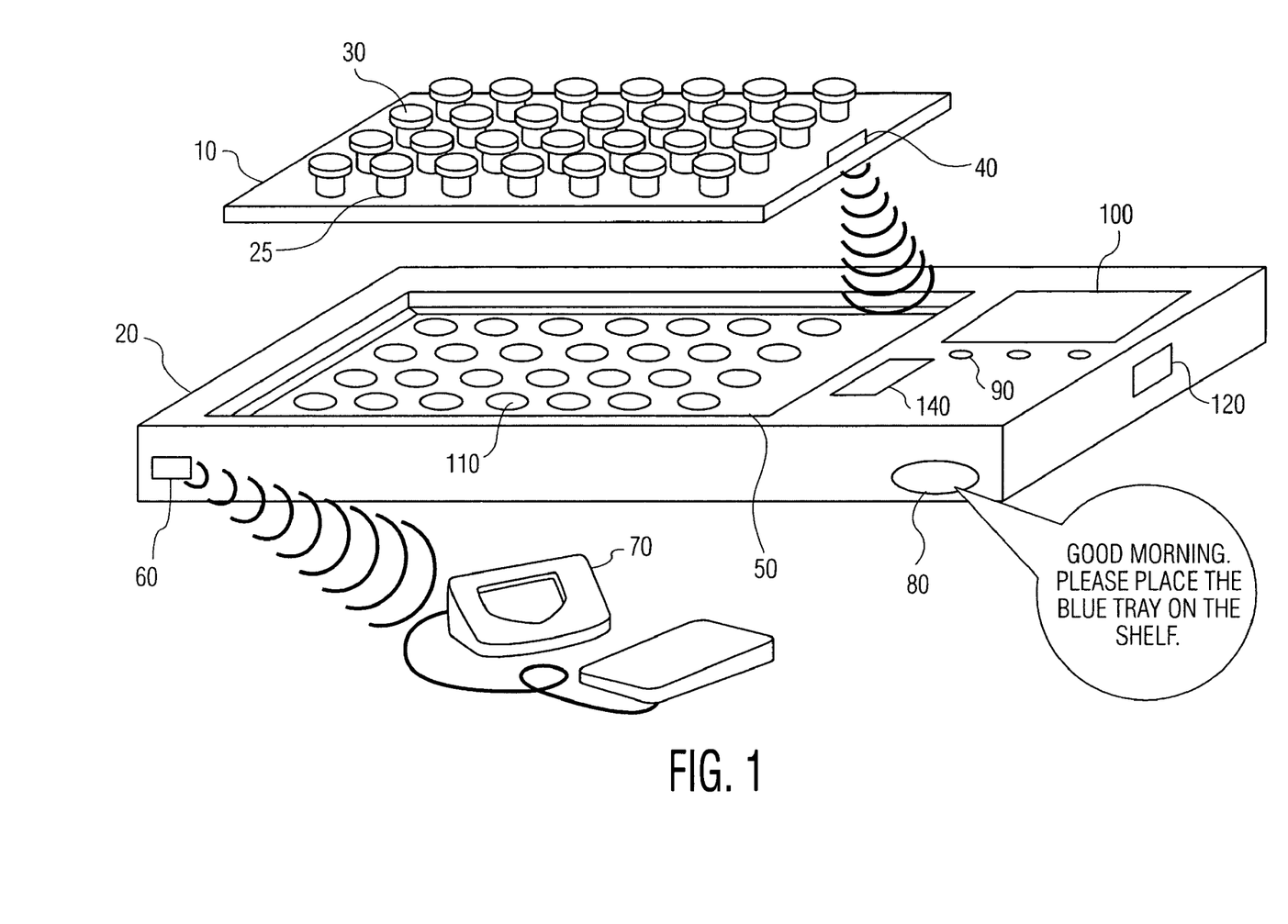
FIG. 1 illustrates a medication adherence system in accordance with an embodiment of the invention.

FIG. 1 illustrates a medication adherence system comprising a smart medication adherence tray 10 (medication tray 10) and a cooperating docking station 20. The smart medication adherence tray 10 contains individual receptacles 25 for receiving removable medication containers 30. The medication tray 10 also contains a means to store information about the medications on the medication tray 10, and a means to communicate this information to the docking station 20. The means to both store this information and communicate it to the docking station 20 will be henceforth referred to as a smart tag. The smart tag is shown schematically at 40 in FIG. 1. The smart tag 40 can use physical data connections, IR, and most preferably, radio frequency (RF) communication methods, all of which are well known to those skilled in the art of the invention.

Medication tray 10 can be used for the automated (or manual) filling of medication orders for patients. Since the medication tray 10 contains medications in an ordered array with defined positions, automated filling and handling of orders is significantly enhanced over concepts intended for filling individual pill containers. At the same time the medication tray 10 is filled, information about the medications and prescription information can be encoded in the smart tag 40 contained in the medication tray 10.

Figure 2A:
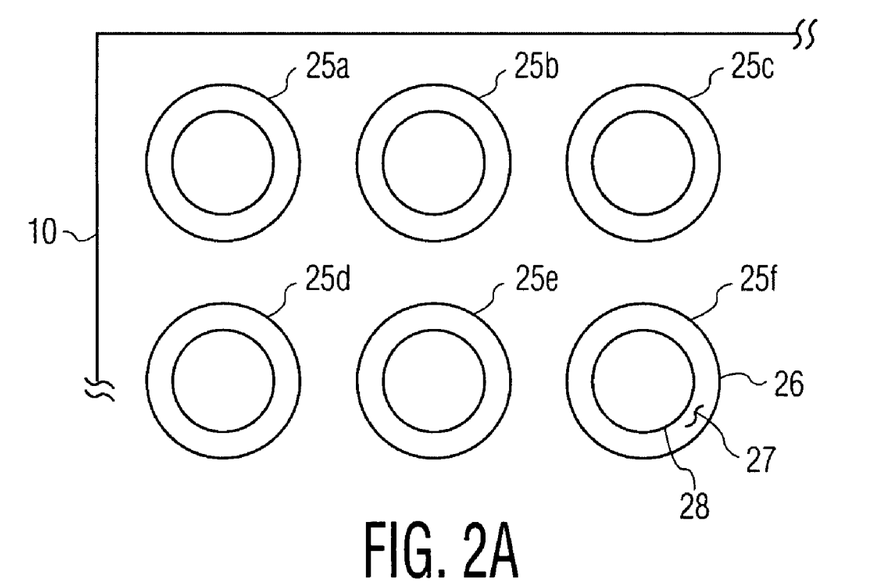
FIGS. 2A and 2B illustrate perspective views of a receptacle in a medication adherence tray in accordance with an embodiment of the invention.
Figure 2B:
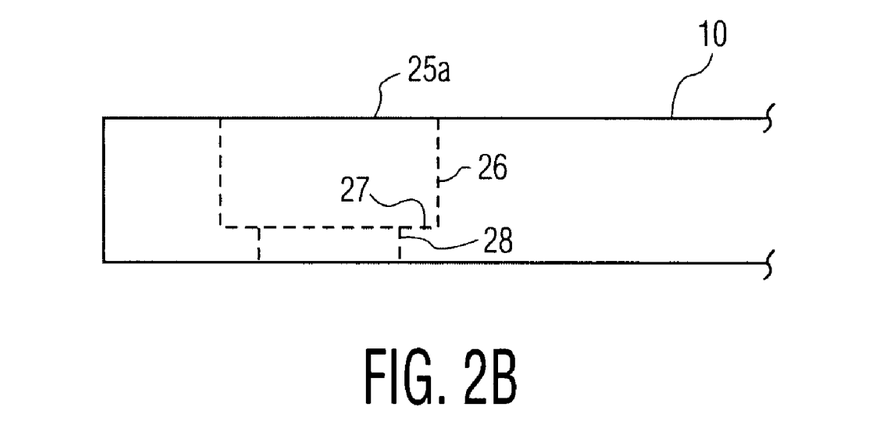

Medication tray 10 is preferably filled by a pharmacist, generic drug provider, or prescription wholesale provider. Specific device configurations and equipment can be used to facilitate automated placement of medications into the medication containers (containers) 30, and of the containers 30 into medication trays 10. FIGS. 2A and 2B illustrate perspective views of a receptacle in a medication adherence tray, in accordance with an embodiment of the invention.

FIG. 2A illustrates that there at least one, and preferably more than one receptacles 25 in tray 10. These are shown as receptacles 25a-25f. FIG. 2B illustrates a side perspective view of receptacle 25a. There is a first hole 26, which preferably extends through most of the depth of tray 10. This provides a secure hold of container 30, when it rests in first hole 26. The mating of receptacle 25 and container 30 is shown and described in greater detail with respect to FIG. 7. Referring back to FIG. 2B, first hole 26 is greater in diameter than second hole 28, which provides for the insertion of the low-bit tags on container 30 to appropriate sensors on docking station 20. The low-bit tags and sensors are described in greater detail below. Because second hole 28 is smaller in diameter than first hole 26, and for design purposes as well, there is a lip 27, upon which the bottom of container 30 will rest when it is inserted into receptacle 25a.

Although an example has been illustrated of a hole-lip design for mating the container 30 with receptacle 25, other designs are possible as well for example, receptacle 25 can be conical in shape such that the wide opening is at the tope of medication tray 10, and the container 30 fits snugly within the cone shaped hole. Or, a press-fit mechanism can be used which allows container 30 to snap into receptacle 25. There are other embodiments of retaining the container 30 which are well known to those skilled in the art of the invention and are considered to be part of the invention.

Figure 3:
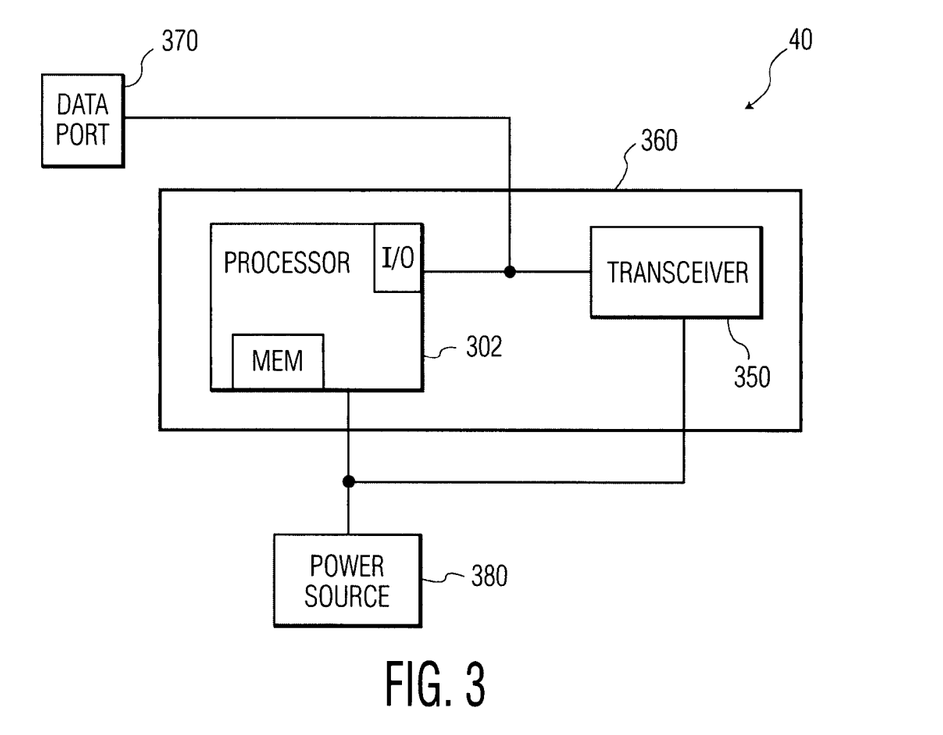
FIG. 3 is a block diagram of a first embodiment of a smart tag transceiver in accordance with an embodiment of the invention.
Figure 4:
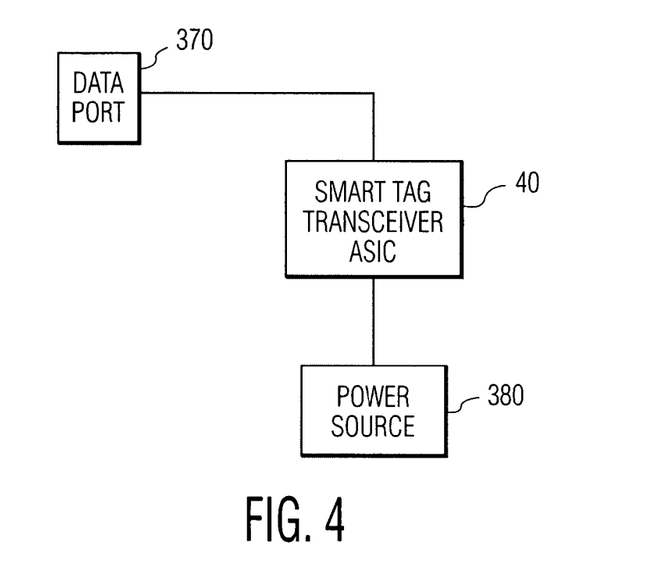
FIG. 4 is a block diagram of a second embodiment of a smart tag transceiver in accordance with an embodiment of the invention.
Figure 5:
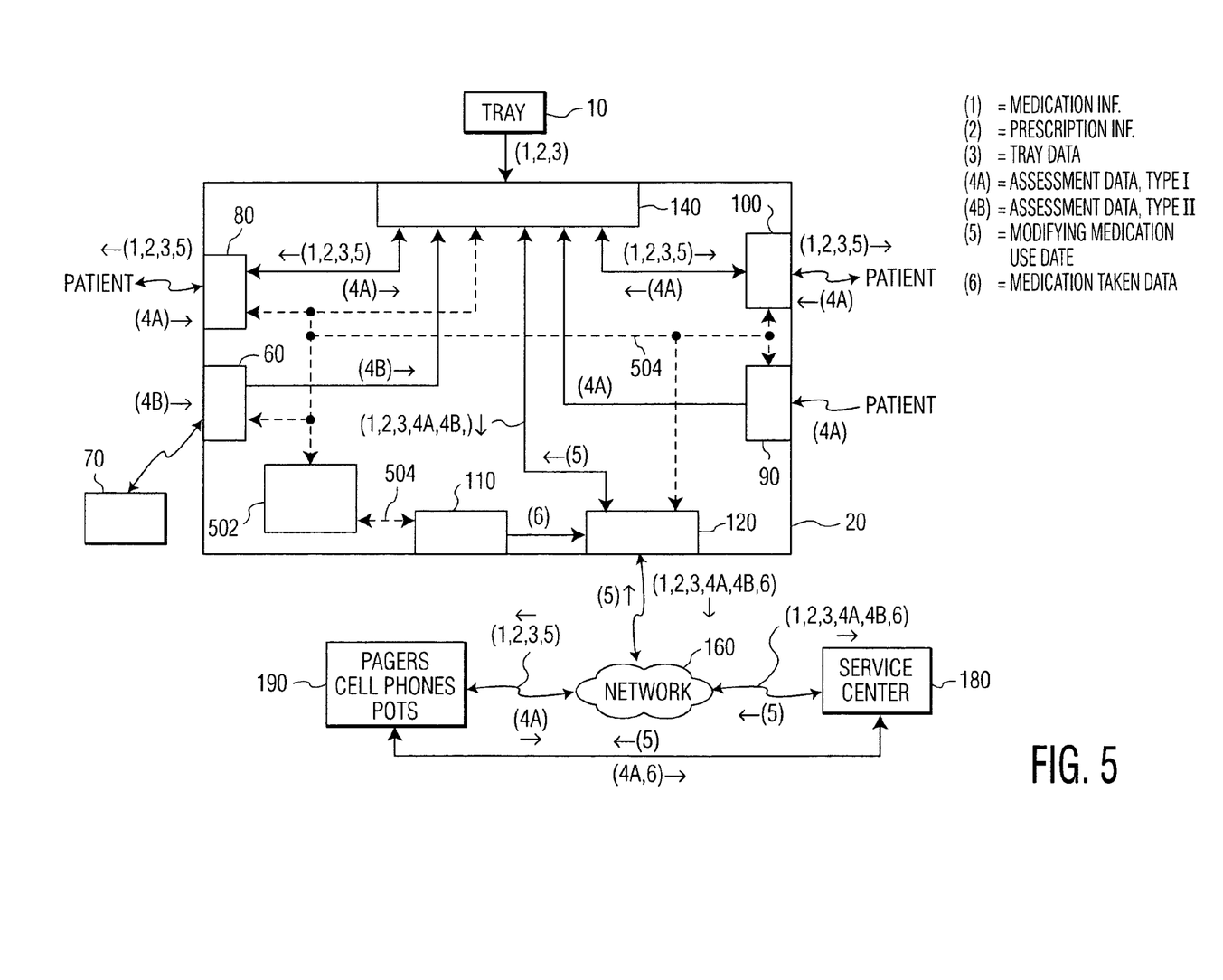
FIG. 5 is a block diagram of a docking station and illustrates data flow within the medication adherence system in accordance with an embodiment of the invention.

Software tools can be used to manage medications, and special processes can be used to ensure high quality in the filling and dispensing process. In this preferred embodiment, multiple prescription patients would be the most advantageous users of the medication adherence system. As the medication tray 10 is loaded with prescription drugs, data about each prescription drug is loaded into the medication tray 10. As shown in FIGS. 3-5, medication information (1), prescription information (2) and tray data (3) can be loaded into the medication tray 10 by one of several different means. The particular mechanism will depend on the configuration of the smart tag 40 transceiver. Medication information (1), prescription information (2) and tray data (3) is collectively referred to as prescription data, and is described in greater detail below.

FIGS. 3 and 4 illustrate a first and second alternative embodiment of a smart tag transceiver system 40 used on a tray 10, in accordance with an embodiment of the invention. In FIG. 3, smart tag system 40 is shown in its component form. There is a transceiver 350, connected to a processor 302, with memory and an I/O port. A power source 380 (which can be a rechargeable cell, standard alkaline cell, or similar type one-time-use-only cell) is connected to the circuit board 360 and then to processor 302 and transceiver 350. Also shown is optional data port 370. Data port 370 is an optional means for receiving data from the device that contains prescription data, when the medicines are loaded into containers, and the containers into tray 10. Optionally, smart tag system 40 can be implemented as an integrated unit (or ASIC) as shown in FIG. 4. There, smart tag system 40 contains a processor, with memory and I/O, but still needs a power source 380, and an optional data port 370. These two embodiments function identically, and are transparent to the user of the medication adherence system.

When prescriptions are loaded into the medication tray 10 (manually or automatically), the operator or loading-system will cause prescription data to be transferred into the medication tray 10, via the smart tag 40 or data port 370. One skilled in the art of the invention can appreciate that the means for transferring data are well known, and the details of such need not be repeated. In accordance with the preferred embodiment, medication information (1), prescription information (2) and tray data (3) can be transferred and stored in the medication tray 10, for later use.

Medication information (1) comprises data about which medications are contained in which container 30, which specific position on the medication tray 10 each container 30 occupies, the time and date the medication is to be taken, information about how to take the medication, and other information commonly found on conventional medication labels, including the date dispensed. Prescription information (2) comprises data which identifies who dispensed and/or prescribed the medications and the name of the facility and/or operator that filled the medication tray 10 and/or containers 30. Additional information can be included for the medication tray 10 as a whole, known as tray data (3), which can include the identity of the individual patient, the range of dates for the medications included on the medication tray 10, expiration or "use by" dates, an identification number unique to that medication tray 10 (e.g., serial number), and the identity of the docking station 20 on which the medication tray 10 is to be placed. Each medication container 30 on the medication tray 10 can contain a single medication or a plurality of different medications to be taken together at the same time, as prescribed by the healthcare service provider (service provider).

Multiple medication trays 10 containing medications can be provided to patients at a single time. For example, a single medication tray 10 can contain medications needed for a single week; however, multiple medication trays 10 containing medications can also be provided so that patients can be supplied for longer periods of time, such as a month. Since these medication trays 10 are uniquely identified through medication information (1), prescription information (2) and tray data (3) encoded in the smart tag 40 on the medication trays 10 when they are filled, patients can be advised of which medication tray 10 to place on the docking station 20 and whether the correct medication tray 10 was placed for the upcoming time period. Medication trays 10 can be scored with frangible connections in order to separate portions of a medication tray 10 in order to travel away from the docking station 20 for limited time periods. These frangible connections can also permit customization of medication trays 10 to individual patient needs.

Referring back to FIG. 1, the docking station 20 contains a receptacle 50 for the medication tray 10, means 140 to communicate with the smart medication tray 10, access to a data network via network communication means 120, a means 60 to communicate with nearby monitoring devices 70, and acoustical, visual or tactile means 80, 90, and 100 to communicate with patients. The docking station 20 also leads the patient to orient the medication tray 10 correctly into the docking station 20. In addition, the medication tray 10 can be organized in a pattern which suggests the correct sequence of medications for the patient.

Once the medication tray 10 is placed on the docking station 20, the docking station 20 communicates with the medication tray 10 to download information contained in the smart tag 40 (i.e., medication (1) and prescription information (2), as well as tray data (3)) via communication means 140. This information is then used to remind patients when to take their medications, inform them about medications, and monitor other assessment information in response to questions asked using the acoustical, tactile or visual means 80, 90, and 100 to communicate with the patient.

FIG. 5 is a block diagram of docking station 20. In docking station 20, microprocessor (processor) 502 communicates with, and handles communications between, acoustical interface means 80, tactile means (push buttons) 90, visual display 100, smart tag communication means 140, network communication means 120 and monitoring device communications means 60. These communications occur over bus 504 (shown as dotted lines).

Data obtained from visual display 100 and touch screens, push buttons and voice recognition software is known as assessment data type 1 (4A). Assessment data type I (4A) are the patient's responses to questions about the patient's health. Acoustical interface means 80 is preferably a speaker/microphone device, with speech synthesis and voice recognition software that resides in processor 502. The speech synthesis software can include pre-recorded audio files of "generic" messages, for example "Please remember to take your medications today." Alternatively, the speech synthesis software can generate detailed messages, with very patient specific information. An example might be "Good Morning Mr. Jones, please take medications A and B before breakfast. How do you feel? Please push the appropriate button visual display 100, or speak your answer into the microphone now." Alternatively, assessment data type I (4A) can be received from the push buttons 90. Questions can also be displayed simultaneously on display 100, or only there, if desired.

A real-time communications link 120 to a service provider 180 center can also be incorporated into the docking station 20. Information about the medications contained in any particular medication container 30 on the medication tray 10 can be displayed on the docking station 20 via visual display 100, thus constituting an electronic label for each medication on the medication tray 10 and docking station 20.

Figure 6:
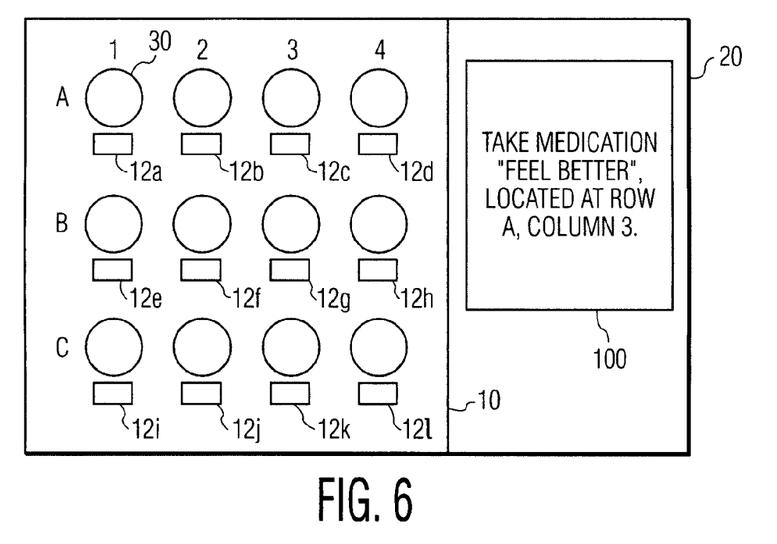
FIG. 6 illustrates a front perspective view of a medication tray and docking station in accordance with an embodiment of the invention.
Figure 7:
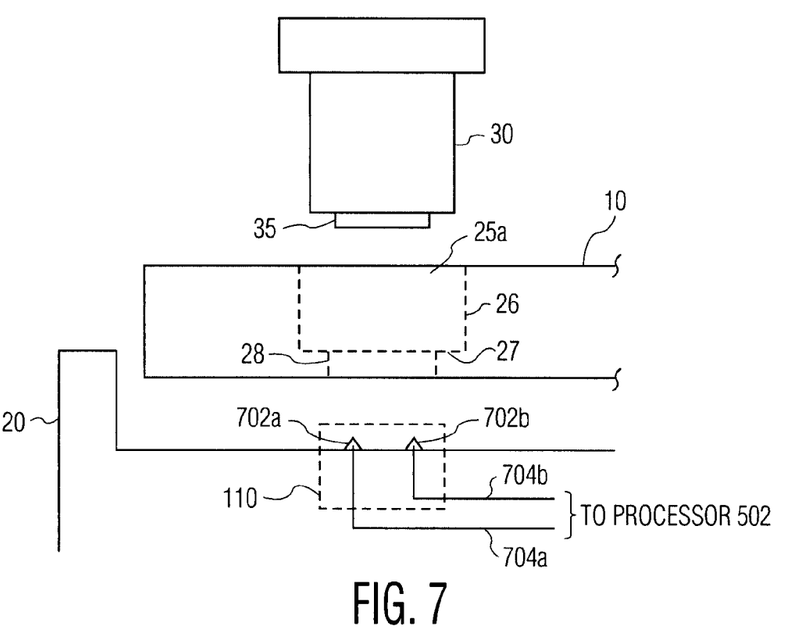
FIG. 7 illustrates the mating of a container in a receptacle of the medication adherence tray and docking station in accordance with an embodiment of the invention.

When the prescribed time to take a medication arrives, the docking station 20 can alert the patient to take a medication using the acoustical, tactile and visual means 80, 90, and 100 or through wireless communications network 160 connectivity via pagers or other wireless devices 190 carried by the patient. This type of data is known as medication use data (and is a subset of medication information (1), described above). Visual means can include lighted indicators 12*a*-121 (see FIG. 6, described in detail below) which identify specific pill bottles 30 to be taken, as disclosed in the aforementioned U.S. Pat. No. 6,294,999. As shown in FIG. 6, patients can see important information on how to take the medications on the visual display 100 of docking station 20, and/or on a personal device (such as a pager) 190. In addition, the docking station 20 contains means 110 to detect when a specific pill container 30 has been removed. These means can include optical sensors, switches, RF tags, or low bit RF tags. This data is known as medication-taken data (6). Medication-taken data (6) is generated by sensors 110, and is used by service center 180 to ascertain the patient's compliance with the patient's medication regime. FIG. 7 illustrates and discusses the sensor 110 and containers 30 in greater detail below.

Referring back to FIG. 5, patients can then remove the indicated container 30 of medications from the medication tray 10, and receive important information about these medications. If a patient removes the wrong container 30, the docking station 20 can alert and guide the patient regarding replacement of the incorrect medication container and selection of the correct medication container. Personal devices can use tactile means (i.e., vibration alerts) to unobtrusively alert patients to take medications; these means are now common on pagers and cellular telephones 190.

The docking station 20 can also communicate with various monitoring devices 70 including, but not limited to, blood pressure meters, weight scales, glucometers, insulin pumps or pens, inhalers, blood chemistries, and peak flow meters. The docking station 20 can prompt use of a monitoring device 70 and use the resulting monitoring information, known as assessment data type 2 (4B), to adjust medication dosage dynamically. Information received by the docking station 20 from the service center 180 regarding dynamic medication dosage adjustment is known as modified medication use data (5). Various medication tray 10 designs can be used to simplify this process. For example, a medication that is adjusted frequently can be placed in a unique position to be taken with each of the other medication containers 30. The docking station 20 can indicate proper dosage of this medication at the prescribed time, and monitor the amount of medications removed from the medication tray 10.

At regular (or irregular) intervals, the docking station 20 can communicate information about patient status through a data network 160 to the service center 180. This information can include the time and identities of medications taken from the medication tray 10 and docking station 20 (part of tray data (3)), whether the correct medication tray 10 was placed on the correct docking station 20, monitoring information from nearby devices 70 that connect to the docking station 20 (assessment data type 2 (4B)), and assessment information from patients' responses to questions presented to them using means resident in the docking station 20 (assessment data type 1 (4A)). The docking station 20 stores this information and then communicates it over a wide area data network 160 to a centralized data store, at service center 180.

FIG. 5 also illustrates data flow within the medication adherence system in accordance with a preferred embodiment of the invention. Medication information (1), prescription information (2) and tray data (3) is initially transferred to medication tray 10, preferably via smart tag 40. Medication tray 10 then transfers data types (1), (2) and (3) to the docking station 20. The docking station 20 can "transfer" data types (1), (2) and (3) to display 100 and acoustical interface means 80. Also, display 100 and acoustical interface means 80 can transfer data type (5), which is modified medication use data (described in detail below), to patients as necessary. Display 100, tactile means 90 and acoustical interface means 80 can also transfer assessment data type 1 (4A) to docking station 20. Assessment data type 2 (4B) is received by communication means 60, and transferred to docking station 20.

Docking station 20 also contains network communication means 120, which provides communications via the network (Internet, LAN, WAN, and similar enterprises of that nature) 160, to a service center 180. Medication taken data (6), and assessment data types 1 and 2 (4A, 4B) can be communicated to the service center 180. Also, medication information (1) can be transferred from the docking station 20, through network communication means 120, to the network 160 and then to pagers, cell phones, telephones or computers 190, to alert patients to take their medicine.

The service center 180 can receive medication taken data (6), medication and prescription information (1, 2), and assessment data types 1, 2 (4A, 4B), from the network 160 connected to the docking station 20. The service center 180 can also receive assessment data type 2 (4B) and medication taken data (6) directly from cell phones, and telephones. The service center 180 can send modified medication use data (5) directly to pagers, cell phones and telephones 190. The service center 180 can also transfer modified medication use data (5) to docking station 20 via the network 160 and network communication means 120.

Once the patient data (assessment data types 1, 2 (4A, 4B) and medication taken data (6)) has been stored, it can be processed so that healthcare providers are more efficient and effective. Healthcare providers can then communicate therapy, monitoring, and behavioral changes (modified medication use data (5)) using the wide area data network 160 back to the patient via the docking station 20, or other devices near the patient, via the network communication means 120. Other devices can include pagers, cell phones, interactive video devices and conventional telephones 190.

FIG. 7 illustrates the mating of a container 30 in a receptacle 25 of the medication adherence tray 10 and docking station 20 in accordance with an embodiment of the invention. The preferred embodiment of the invention utilizes a RF smart tag 40 on the medication tray 10 and inexpensive "low bit" tags 35 on each medication container 30. "Low bit" tags 35 refer to very inexpensive tags and readers that indicate only whether the container 30 is present and contain little information about the container contents. There are significant cost savings associated with this approach, since the combination of many low bit tags 35 and a single smart tag 40 is much less than the cost of placing a smart tag 40 on each medication container 30. Since the medication tray 10 has "learned" the location of each container 30 and its contents when they were placed in the medication tray 10, and corresponding data downloaded, medication taken data (6) is easily determined by the docking station 20 when the patient retrieves the container 30 from the medication tray 10.

The detector 110, in one embodiment, is comprised of probes 702*a* and 702*b*, to which are connected wires 704*a* and 704*b* respectively. These wires 704*a* and 704*b* are then connected to processor 502. As one skilled in the art of the invention can appreciate, these wires can also be circuit board runs, or micro-strips. The diameter of container 30 is just smaller than the diameter of first hole 26. This allows for a snug, but not too tight fit of container 30 into receptacle 25*a* The low-bit tag 35 fits through second hole 28, which is smaller than first hole 26, which provides for lip 27, upon which the bottom of container 30 will rest when it is inserted into receptacle 25*a* When container 30 is placed into receptacle 25*a*, low-bit tag 35 comes into contact with probes 702*a* and 702*b*. In a preferred embodiment, low-bit tag 35 is made of metal, and can allow a low voltage, low current signal to be conducted through it, which processor 502 can sense. Similarly, when container 30 is removed from receptacle 25, processor 502 senses the breaking of the connection by the absence of the signal, and recognizes the particular container's 30 removal. This records, for example, that the container 30 located at row A, column 4, has been removed (see FIG. 6). If the patient removes the wrong container 30, the docking station 20 can alert the patient of his or her mistake, by flashing a lamp 12a in a red color, along with an audio alert. In addition to the low bit tags 35 already described, mechanical switches and optical sensing devices such as silicon photodiodes or CCDs can be used as sensors 110 to determine the presence or absence of a medication container 30. Also, the low-bit tags 35 can be RF tags, and the sensors 110 can be an RF transceiver, similar to the smart tag system 40.

While FIG. 1 shows many medication container receptacles 25, the number of receptacles 25 will be dictated by the complexity of the patient's disease state. Devices of various sizes can be used to match the needs of patients with different diseases and disabilities. These devices can have different user interfaces for communication as described above. Visual displays 100 can include touch screens, LCDs, electroluminescent displays, conventional CRT displays, and E-ink technologies. Numerous technologies exist for the smart tag 40 and smart tag reader 140. These include various RF methods, optical communications (e.g., optocouplers), and physical serial connections.

Visual cues to identify individual medication containers 30 can include the use of light emitting diodes or lasers of various colors, and light pipe configurations on the medication tray 10. Organic diodes and electroluminescent methods, or E-ink, as developed by the MIT Media Lab, can also be convenient and low-cost methods of identifying individual pill containers 30. In addition to light emission, the use of shape and color will also assist patients as they take medications. Connection to an external data network can include well-known methods such as RF, including 802.11 and Bluetooth standards, IRDA, various wireless data systems including pager networks, cellular packet data, and 2G and 3G systems, and physical serial connections such as the USB or Firewire standards.

Figure 8:
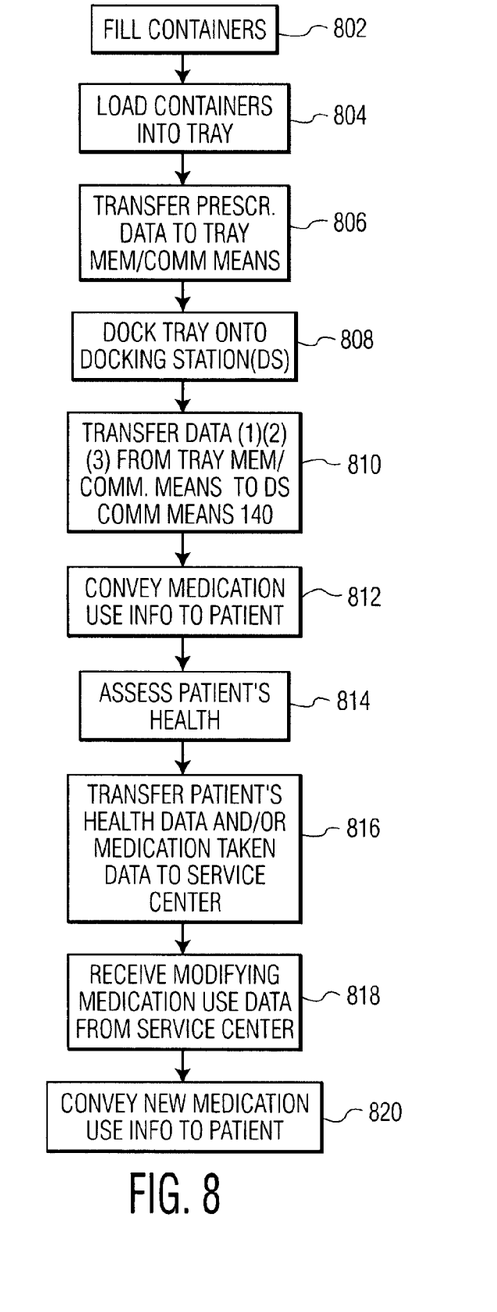
FIG. 8 illustrates a flow diagram of a method for utilizing the medication adherence system in accordance with an embodiment of the invention.

FIG. 8 illustrates a flow diagram of a method for utilizing the medication adherence system in accordance with an embodiment of the invention. The method of FIG. 8 begins with step 802, in which the containers 30 are filled with medicine. After being filled with medicine, the containers 30 are then loaded into a medication tray 10, preferably in an order which is conducive to adherence to a medication regimen. Prescription data is then transferred, in step 806 to the medication tray 10, via smart tag system 40, or data port 370, where it is stored in a memory, as described in detail above. The medication tray 10 is then shipped to a patient, or distributed to a pharmacy (whether at a hospital, urgent medical care facility or similar institution), and obtained by the patent. The patient will then dock the medication tray 10 into docking station 20 (step 808). The action of docking causes prescription data to be automatically transferred from the medication tray 10 to docking station 20, via smart tag system 40 and means 140 (preferably a smart tag reader) for communicating with the smart tag system 40. The prescription data is stored in suitable memory means.

Once the prescription data is stored in memory means in docking station 20, processor 502 ascertains the medication regime, either from the prescription data, or from communications received from a service center 180, and begins, at the appropriate times and manner, to alert the patient to take the medications as directed (step 812). Docking station 20 verifies that the proper medications are being taken, at the proper times, and as much as possible, in the proper manner. At some point, docking station 20 can query the patent to ascertain his or her health and obtain assessment data (step 814). As discussed above, there are different types of assessment data, and these are collected and processed by the docking station 20. The collected and processed assessment data can then be transferred to the service center 180 in the manner described more fully above (step 816). If necessary, in step 818, the service center 180 can send modifying medication use data to the docking station 20, and change (or not) the medication regime for the patent. The information received from the service center 180 can also be instructions to obtain further or a different type of assessment data, or a combination of these. Finally, in step 820, new medication use information can be conveyed to the patient, in the various different methods already described. The method described in FIG. 8 is but a brief summary of the steps more fully described in the preceding paragraphs.

The use of defined medication and disease management protocols will assist healthcare providers in interacting with the medication adherence system of the present invention. The medication adherence system of the present invention can significantly reduce the time required to optimize and customize therapies for patients. The invention fulfills many of the unmet needs described above, and represents a significant improvement in patient care.

The present invention has been described with reference to certain exemplary embodiments thereof. However, it will be readily apparent to those skilled in the art that it is possible to embody the invention in specific forms other than those of the exemplary embodiments described above. This can be done without departing from the spirit and scope of the invention. The exemplary embodiments are merely illustrative and should not be considered restrictive in any way. The scope of the invention is defined by the appended claims and their equivalents, rather than by the preceding description.

We claim:

1. A medication adherence system, comprising:
   a medication adherence tray adapted to comprise a first communication means for receiving prescription data from a prescription data storage device and transmitting it to the docking station;
   a docking station adapted to receive the medication adherence tray and comprise the first communication means for communicating with the medication adherence tray the prescription data and a second communication means for detecting the insertion, removal and replacement of one or more medication filled containers; and
   one or more medication filled containers, the one or more medication filled containers comprising a sensor tag.

2. The medication adherence system according to claim 1, wherein the medication adherence tray further comprises:
   one or more receptacles for receiving the medication filled containers.

3. The medication adherence system according to claim 1, wherein the docking station further comprises:
   a patient communication means for communicating prescription data to a patient.

4. The medication adherence system according to claim 1, wherein the first communication means comprises:
   a smart tag RF transceiver, serial data port or IR communications link.

5. The medication adherence system according to claim 1, wherein the prescription data comprises:
   medication information;
   prescription information; and
   tray data.

6. The medication adherence system according to claim 5, wherein the medication information comprises:
   identity of one or more medicines in the container, a position in the medication adherence tray the container occupies, time and date information for the patient taking the medication and/or directions as to how to consume the one or more medications.

7. The medication adherence system according to claim 5, wherein the prescription information comprises:
   a name of a person who prescribed the medication, a name of a person who dispensed the medication into the one or more containers, and/or a name of a facility where the container was filled.

8. The medication adherence system according to claim 5, wherein the tray data comprises:
   a patient name, range of dates for use of the medications, expiration dates, an identification number of the medication adherence tray and/or an identification number of the docking station.

9. The medication adherence system according to claim 1, further comprising:
   a third communication means to receive prescription data from the prescription information storage device.

10. The medication adherence system according to claim 9, wherein the third communication means comprises:
    a serial data port.

11. The medication adherence system according to claim 1, wherein the second communication means comprises:
    container presence sensor means.

12. The medication adherence system according to claim 3, wherein the patient communication means comprises:
    at least one of an acoustical interface means, tactile communication means, network interface communications means associated with patient communication devices and visual display means.

13. The medication adherence system according to claim 1, further comprising:
    patient monitoring device communications means.

14. The medication adherence system according to claim 13, wherein the patient monitoring devices comprises:
    blood glucose level meters, heart rate monitors, blood pressure monitors, scales, insulin pumps, inhalers, blood chemistry analyzers and/or peak flow meters.

15. The medication adherence system according to claim 13, wherein the patient monitoring devices communications means comprises:
    RF, IR, Bluetooth, data port and/or smart tag.

16. The medication adherence system according to claim 12, wherein the medication adherence trays are frangible.

\* \* \* \* \*